United States Patent [19]

Ortega et al.

[11] Patent Number: 5,408,868
[45] Date of Patent: Apr. 25, 1995

[54] METHOD AND APPARATUS FOR OBTAINING ON-LINE GAS SAMPLES FOR THE MEASUREMENT OF CRUDE OIL CONTENT

[75] Inventors: Pedro Ortega, Los Teques; Fernando Cassani, San Antonio de Los Altos; Enrique Poleo; Daniel Fernandez, both of Los Teques, all of Venezuela

[73] Assignee: Intevep, S.A., Caracas, Venezuela

[21] Appl. No.: 172,759

[22] Filed: Dec. 27, 1993

Related U.S. Application Data

[62] Division of Ser. No. 928,289, Aug. 12, 1992, Pat. No. 5,301,536.

[51] Int. Cl.⁶ ...................... B01D 39/16; G01F 15/08
[52] U.S. Cl. .................................. 73/61.41; 73/31.07; 55/228
[58] Field of Search ............... 73/61.41, 31.07, 23.38, 73/61.44; 55/274, 228, 259, 159

[56] References Cited

U.S. PATENT DOCUMENTS

| | | | |
|---|---|---|---|
| Re. 31,849 | 3/1985 | Klein | 55/389 |
| 3,985,624 | 10/1976 | Prevost et al. | 196/132 |
| 4,004,453 | 1/1977 | Thyrum | 73/61.1 R |
| 4,215,567 | 8/1980 | Vlcek | 73/61.1 R |
| 4,386,534 | 6/1983 | Englund et al. | 73/863.01 |
| 4,629,476 | 12/1986 | Sutt, Jr. | 55/68 |
| 4,715,868 | 12/1987 | Kennedy | 55/48 |
| 4,760,742 | 8/1988 | Hatton | 73/861.04 |
| 4,772,295 | 9/1988 | Kato et al. | 55/16 |
| 5,196,380 | 3/1993 | Shadman | 502/4 |
| 5,301,536 | 4/1994 | Ortega et al. | 73/31.07 |

Primary Examiner—Hezron E. Williams
Assistant Examiner—J. David Wiggins
Attorney, Agent, or Firm—Bachman & LaPointe

[57] ABSTRACT

The present invention is drawn to a method for measuring crude oil contained in a gas flowing in a gas line which incorporates the steps of obtaining a sample of gas from the gas line, passing the sample of gas through a selective crude oil trap, measuring the volume of the sample of gas, and measuring the volume of trapped crude oil. The selective crude oil trap includes a cooled coil and at least one cylinder filled with a fluid which is non-soluble with oil and which is preferably refrigerated. The selective crude oil trap may alternatively include a filter device which has a cylinder filled with a polymerized porous medium bound with a phenolic resin. The apparatus for carrying out the method has inlet and outlet connectors which allow the apparatus to be releasably connected to a gas flow line to obtain a sample of gas and to be disconnected and physically transported to a remote facility for completion of the testing.

9 Claims, 2 Drawing Sheets

METHOD AND APPARATUS FOR OBTAINING ON-LINE GAS SAMPLES FOR THE MEASUREMENT OF CRUDE OIL CONTENT

This is a division of application Ser. No. 07/928,289, filed Aug. 12, 1992, now U.S. Pat. No. 5,301,536.

BACKGROUND OF THE INVENTION

The invention relates to the field of gas pipelines, and, more particularly, to a method and apparatus for obtaining on-line gas samples and measuring these samples for crude oil content.

DESCRIPTION OF THE RELATED ART

An important aspect in maintaining gas lines for transportation of hydrocarbon gas is the control of crude oil entrained with the gas. While the gas is routinely treated with scrubbers and various other equipment in order to remove liquids such as crude oil, carry over of crude into the gas lines after such treatment still occurs with some regularity. Further, numerous problems are caused by such carry over of crude because gas lines and equipment are not intended for use with liquids, and crude oil can adhere to walls of gas lines and other equipment and impair performance. Detection and quantification of crude oil entrained in a flow of gas in a gas line is therefore of appreciable importance.

U.S. Pat. No. 4,760,742 to Hatton discloses a method whereby a separator is used to break a stratified flow of fluids into liquid and gas components and the volume of each is measured. Such a system therefore provides a measure of total liquids to gas. Since crude oil specifically causes more problems than other liquids entrained with the gas, however, it is desirable to be able to quantify, specifically, the volume of crude oil entrained with the gas.

Other disclosed techniques involve the use of gas chromatography and/or gamma radiation to quantify the fluids flowing in a stream of gas or oil. These techniques, however, are sophisticated and thus limited in their application, and also do not provide a specific quantification of crude oil entrained in the gas.

Systems such as those disclosed in aforesaid U.S. Pat. No. 4,760,742 entail substantial installations on-site at the gas line in order to test a flow of gas and entrained liquids. It is desirable, however, to provide a system for specifically quantifying crude oil entrained in a gas line which is simple in construction and use and which can be readily used to test gas lines in more than one location.

Accordingly, it is the principal object of the present invention to provide a system whereby the volume of crude oil contained in a stream of gas can be specifically and selectively quantified.

A further object of the present invention is to provide an apparatus which can be connected to a gas line to obtain a sample of gas, and disconnected for transport to a remote laboratory facility for testing and measurement.

A still further object of the present invention is to provide an apparatus for selective measurement of crude oil which is simple in manufacture and operation and does not require sophisticated techniques.

Further objects and advantages of the present invention will appear hereinbelow.

SUMMARY OF THE INVENTION

In accordance with the present invention, the foregoing objects and advantages are readily obtained.

The present invention is drawn to a method for measuring crude oil contained in a gas flowing in a gas line by measuring the volume of crude oil contained in a sample of the gas, which comprises the steps of: obtaining a sample of gas from the gas line; passing the sample of gas through means for selectively trapping crude oil so as to trap substantially all crude oil contained in the sample of gas; measuring the volume of the sample of gas; and measuring the volume of trapped crude oil.

According to a preferred embodiment of the invention, the selected trap means comprises means for cooling the sample of gas and at least one cylinder containing filter means for selectively trapping crude oil.

The cooling means preferably comprises a coil submerged in a refrigerated bath. The sample of gas is passed through this coil in order to provide cooling which alters the solubility of the gas and crude oil and facilitates the selective trapping of crude oil.

A plurality of cylinders are preferably connected to the gas inlet in series after the cooling means. At least one of the cylinders, preferably the first one in series, is refrigerated and is partially filled with a liquid which is non-soluble to oil as the filter means. The liquid in at least one cylinder may be water which traps crude oil as the sample of gas flows through the cylinder.

After a sample of gas has been passed through the selective trap means, the volume of crude oil trapped by the trap means is measured, and compared to the volume of the sample of gas in order to obtain a representative measurement of crude oil contained in the gas flowing in the gas line.

According to an alternate embodiment of the invention, the selective trap means comprises a filter device having a cylinder filled with a porous medium through which the sample of gas is passed in order to trap the crude oil.

According to still another embodiment, a gas inlet of the selective trap means is attached to the gas line through means for releasably connecting the trap means to the gas line, whereby the selective trap means can be connected to the gas line to obtain the sample of gas and the selective trap means can be disconnected from the gas line and transported to a remote facility for measurement of volume of trapped crude oil.

The method and apparatus of the present invention allow selective quantification of the volume of crude oil entrained in a sample of gas obtained from a gas line. The effectiveness of this quantification will be made clear hereinbelow from a reading of the detailed description.

BRIEF DESCRIPTION OF THE DRAWING

A detailed description of a preferred embodiment of the invention follows, with reference to the attached drawings, in which.

DETAILED DESCRIPTION OF THE INVENTION

Figure 1:
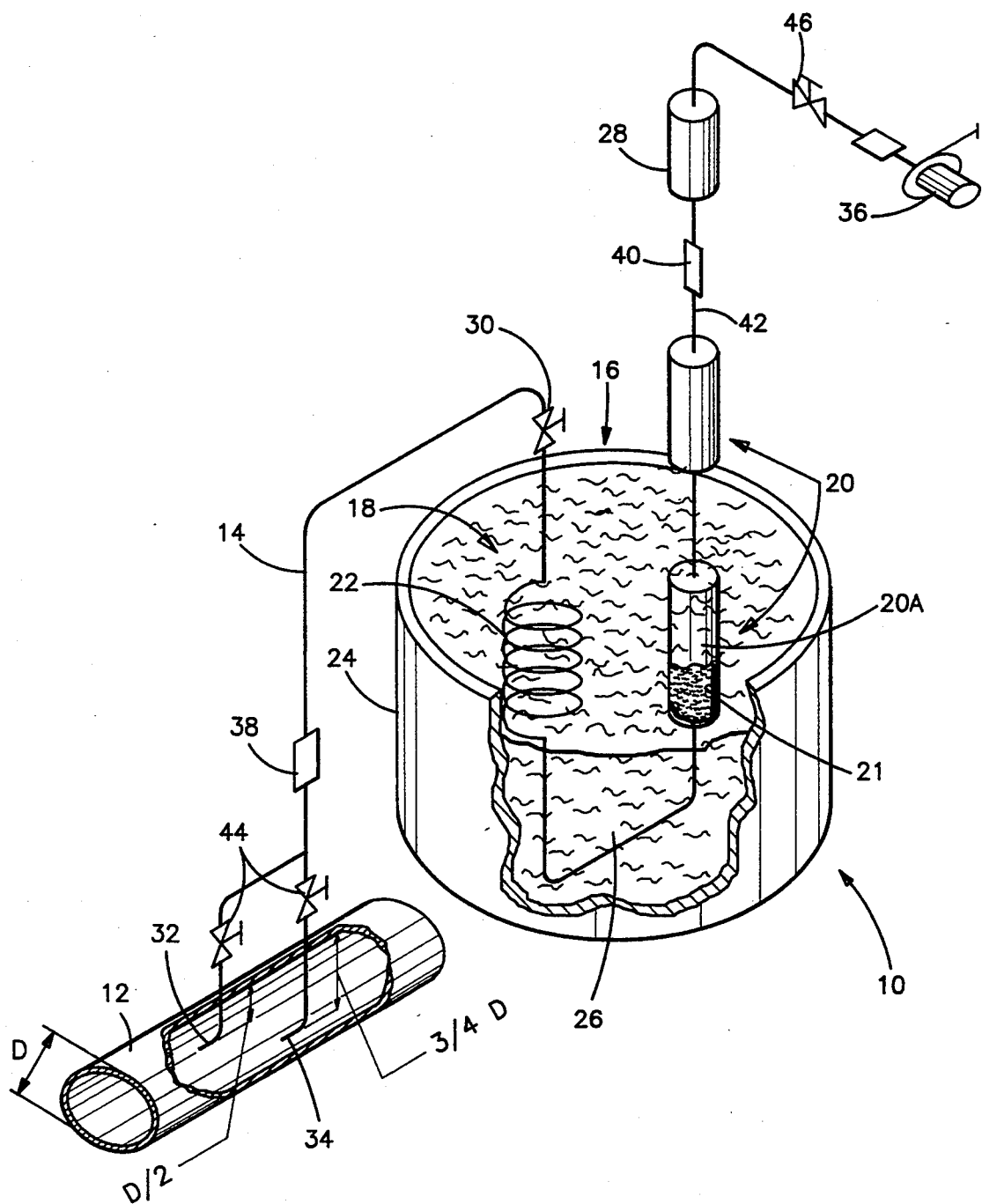
FIG. 1 is a perspective and partially cut away view of an apparatus for measuring crude oil, according to the invention, in its environment.

The present invention is drawn to a method and apparatus for selectively quantifying the volume of crude oil entrained in gas flowing in a gas line.

This volume is determined by selectively quantifying the volume of crude oil contained in a representative gas sample obtained from the gas line.

The method of the invention comprises the steps of obtaining a sample of gas, passing the sample of gas through means for selectively trapping crude oil, measuring the volume of trapped crude oil, and measuring the volume of the sample of gas.

The sample of gas is obtained from a gas line through any means known in the art which will provide an accurate representative sample of the gas.

A cross section of various techniques used to take a representative sample from a gas line is outlined in a paper entitled *Methods For Obtaining Natural Gas Samples For Analysis By Gas Chromatography* issued by the Gas Processors Association as GPA publication No. 2166-68, the text of which is incorporated herein by reference.

According to the invention, the gas sample is passed through trap means to selectively trap crude oil contained in the gas sample.

As used herein, selective trap means refers to a structure which can be used to selectively trap hydrocarbon liquids contained in the sample of gas so that the volume of trapped hydrocarbon liquids can then be measured. As used herein, selective trapping refers to trapping hydrocarbon liquids to the exclusion of other liquids, such as water, which are not to be measured. Descriptions of several preferred embodiments of selective trap means follow. These preferred embodiments operate by trapping crude oil in such a way that the volume of crude oil or hydrocarbon liquids can be measured to the exclusion of other liquids which may or may not be trapped with the crude oil.

According to a first preferred embodiment, the gas is transmitted to a cooling means and thence to at least one trap cylinder. While the structure of these elements will be more fully described below, their function, as relevant to this method, is to cool the gas to a temperature, preferably in the range of about 0°–10° C. (32°–50° F.), thereby affecting the solubility of the gas and crude oil, and then to selectively trap crude oil by passing the gas through a volume of cooled liquid, contained in at least one of the trap cylinders, which cooled liquid is nonsoluble to oil. A suitable non-oil-soluble liquid may, for example, be water. Crude oil is trapped while passing through the cooled non-oil-soluble liquid and settles in a layer over the liquid. This trapped crude oil can be drawn from the cylinder for measurement through any conventional means for separating oil and gas and may, for example, be skimmed from the top of the non-oil soluble liquid.

Since trapped oil may be adhered to flow elements of the test apparatus, and the measurement of trapped crude oil must be accurate, the volume of trapped crude oil is preferably measured by flushing the test apparatus with a known initial volume of a solvent, such as toluene, and then measuring the final volume of toluene and crude oil. The difference is a volume of trapped crude oil which, when added to the volume of crude oil separated from the liquid in the trap cylinders, yields an accurate measurement of the total volume of trapped crude oil.

The trap means, according to the invention, is preferably connected to the gas line through means for releasably connecting a gas inlet to the gas line. The structure of the connecting means is not critical, and could be any structure known in the art for releasably connecting two flow conductors. This structure is preferably as simple and easy to operate as possible.

The connecting means serves to allow the trap means to be connected to a gas line to obtain a sample on-site, after which the trap means can be disconnected and transported to any testing facility or laboratory where the volume of trapped crude oil can be accurately measured. Thus, obtaining samples according to the invention does not require extensive on-site installations as in the afore-described U.S. Pat. No. 4,760,742.

The volume of the sample of gas is measured through any means known in the art, such as a flow meter through which the gas sample is passed, or a storage container into which the gas sample is introduced.

It should be noted that the accuracy of results obtained by this method is dependent upon a trapping of substantially all crude oil contained in the gas sample. To this end, the method preferably includes the step of passing the gas sample through a means for detecting crude oil, after the gas sample has been passed through the trap means. Preferable structure of the crude oil detecting means will be described below, the function of the oil detecting means as relevant to this method being to ascertain, through any means known in the art, that the processed gas sample no longer contains crude oil, that is, substantially all hydrocarbon liquids have been trapped.

According to an alternate embodiment of the invention, crude oil is trapped by passing the gas sample through a cylinder containing a polymerized porous medium having a mesh size in the range of about 12–16.

The porous medium traps crude oil both by absorbance and through mechanical entrapment in the pore space of the porous medium. Thus, according to this embodiment, the volume of trapped crude oil is measured as follows.

The cylinder is flushed with a known initial volume of solvent such as toluene to determine the volume of crude oil trapped in the porous medium.

The volume of trapped crude oil which was absorbed can be measured through a UV-visible spectrometer at a wave length of approximately 500 nm. The obtained absorbancy value is checked on a calibration curve to yield the amount of oil absorbed by the resin.

Total trapped crude oil is then obtained by adding the aforesaid volumes.

In either of the foregoing embodiments, the volume of trapped crude oil and of the gas sample can be corrected through familiar pressure-volume-temperature calculations to obtain the volume of trapped crude oil at desired temperature and pressure and in useful form such as, for example, barrels of crude oil per MM cubic feet of gas.

FIG. 1 shows a preferred embodiment of an apparatus 10 for measuring crude oil in a sample of gas, according to the invention, attached to a gas line 12 from which a sample is to be obtained and tested.

Apparatus 10 preferably includes a gas inlet 14 to which is attached a means 16 for selectively trapping substantially all crude oil.

The method and apparatus of the present invention selectively trap substantially all crude oil. In other words, crude oil is trapped and measured to the exclusion of other liquids whereby a ratio of crude oil to gas can be obtained. This is in contrast to known methods as described above wherein a ratio of total liquid to gas is determined.

Selective trap means 16 may preferably comprise a cooling means 18 connected to gas inlet 14, and at least one trap cylinder 20. Cooling means 18 preferably comprises a coil 22 submersed in a refrigerated fluid 26 which may be contained in any suitable container 24. Coil 22 is connected to gas inlet 14 so that the gas sample is cooled as it flows through the coil. Any type of coil structure is suitable which will provide the desired cooling. A preferable coil is a coil of cyclone type. Refrigerated fluid 26 preferably comprises water refrigerated to a temperature of about 0°–10° C. (32°–50° F.) or any other fluid which can be maintained as liquid at the indicated temperature.

Coil 22 is further preferred as cooling means 18 because it provides cooling to the aforesaid temperature in a rapid and space efficient manner.

A plurality of trap cylinders 20 are preferably connected in series after coil 22. The first trap cylinder 20A of the serially arranged plurality is preferably partially filled with a fluid which is non-soluble with crude oil. Such a fluid may preferably be water in a volume of about ⅓ of the first trap cylinder 20A. The first trap cylinder 20A is also preferably refrigerated to a temperature of between about 0°–10° C. (32°–50° F.). This is most simply and preferably accomplished by submerging the first trap cylinder 20a in the refrigerated fluid 26.

Subsequent trap cylinders 20 may, but need not, contain water or be refrigerated as is first trap cylinder 20A. The primary function of subsequent trap cylinders 20 is to catch any crude oil which may bubble up through first trap cylinder 20A.

This embodiment operates as follows. Trap means 16 is connected to gas line 12 through connector means 38, 40. A gas sample is obtained from gas line 12 and flows to gas inlet 14. The gas line conditions of the gas are generally in the range of about 71°14 93° C. (160°–200° F.) and about 3.0 atmospheres. This gas sample flows to coil 22 where the gas sample is rapidly cooled to a temperature of about 0°–10° C. (32°–50° F.).

From coil 22, the cooled gas sample flows to first trap cylinder 20A, where fluid 21 contained in first trap cylinder 20A traps substantially all crude oil contained in the gas sample. Because fluid 21 in trap cylinder 20A is non-soluble with oil, trapped crude oil forms in a layer on the surface of fluid 21 where, as stated previously, it may be separated from the non-oil-soluble liquid through any conventional means.

Any crude oil which bubbles up through first trap cylinder 20A is trapped by subsequent trap cylinders 20.

The volume of trapped crude oil may be determined as follows. Fluid 21 and trapped crude oil are removed from trap cylinders 20, and entire trap means 16 is flushed with a known initial volume of a solvent such as toluene. The volume of trapped crude oil is then determined by adding the volume of oil measured from the surface of fluid 21 and the volume flushed by the solvent.

The volume of the gas sample is then determined through any means known in the art and as more fully described below.

The volumes of crude oil and gas so obtained can then be corrected through well known pressure-volume-temperature calculations to obtain an expression of crude oil per gas, such as barrels of crude oil per MM cubic feet of gas, at desired pressure and temperature conditions.

It is important to verify that substantially all crude oil contained in the gas sample is trapped. To this end, a visual control element 28 may preferably be disposed along gas line 12, in series after selective trap means 16.

Visual control element 28 may comprise, for example, a filter element that changes color in the presence of crude oil, or any other means for verifying substantial entrapment of crude oil.

It has been found that trap means 16 functions better to trap crude oil if the cooling function is achieved in a sudden manner. Accordingly, an inlet control valve 30 is preferably disposed between gas inlet 14 and coil 22 so that the gas sample can be delivered to coil 22 by opening control valve 30.

As previously mentioned, the gas sample is obtained through any means known in the art, such as, for example, the methods described in aforesaid GPA pub #2166-68. In order to compensate for stratified or layered flow of gas and crude oil, the gas sample is preferably obtained through a plurality of sample collectors 32, 34, located at various locations in gas line 12. FIG. 1 shows one collector 32 located at a distance from the top of gas line 12 equal to one half of the diameter D of gas line 12. Another collector 34 is disposed at a distance of three-fourths of the diameter from the top of gas line 12.

Obviously, as many collectors as are both practical and necessary could be used to assure an accurate gas sample.

The volume of the gas sample may be determined by any means for measuring a flowing volume of gas such as, for example, a gas meter 36 as shown in FIG. 1. Alternatively, the volume of the gas sample could be measured by introducing the sample into a storage container of known volume and measuring the resulting pressure in the storage container.

The apparatus according to the invention can preferably be releasably attached to a gas line to collect a gas sample, and can then be disconnected for transport to laboratory facilities for testing and measuring. To this end, apparatus 10 preferably includes an inlet connector 38 disposed at the end of gas inlet 14, and an outlet connector 40 disposed at the end of a gas outlet 42 of apparatus 10. In this embodiment, inlet connector 38 is attached to collectors 32, 34 to obtain the gas sample. While the sample is being obtained, outlet connector 40 is connected to aforesaid measuring means such as gas meter 36. When the gas sample is obtained, connectors 38, 40 are disconnected and apparatus 10 is preferably transported to laboratory facilities (not shown) where connectors 38, 40 facilitate the toluene flushing and other procedures involved in determining the volume of trapped crude oil. Connectors 38, 40 may be any type of connector for tubular flow conductors, and are preferably of a type which is quickly and easily operated. Inlet valves 44 may be disposed between inlet connector 38 and collectors 32, 34 to prevent escape of gas from the gas line during connection and disconnection of apparatus 10.

An exhaust valve 46 may be disposed at any convenient location along gas outlet 42.

Figure 2:
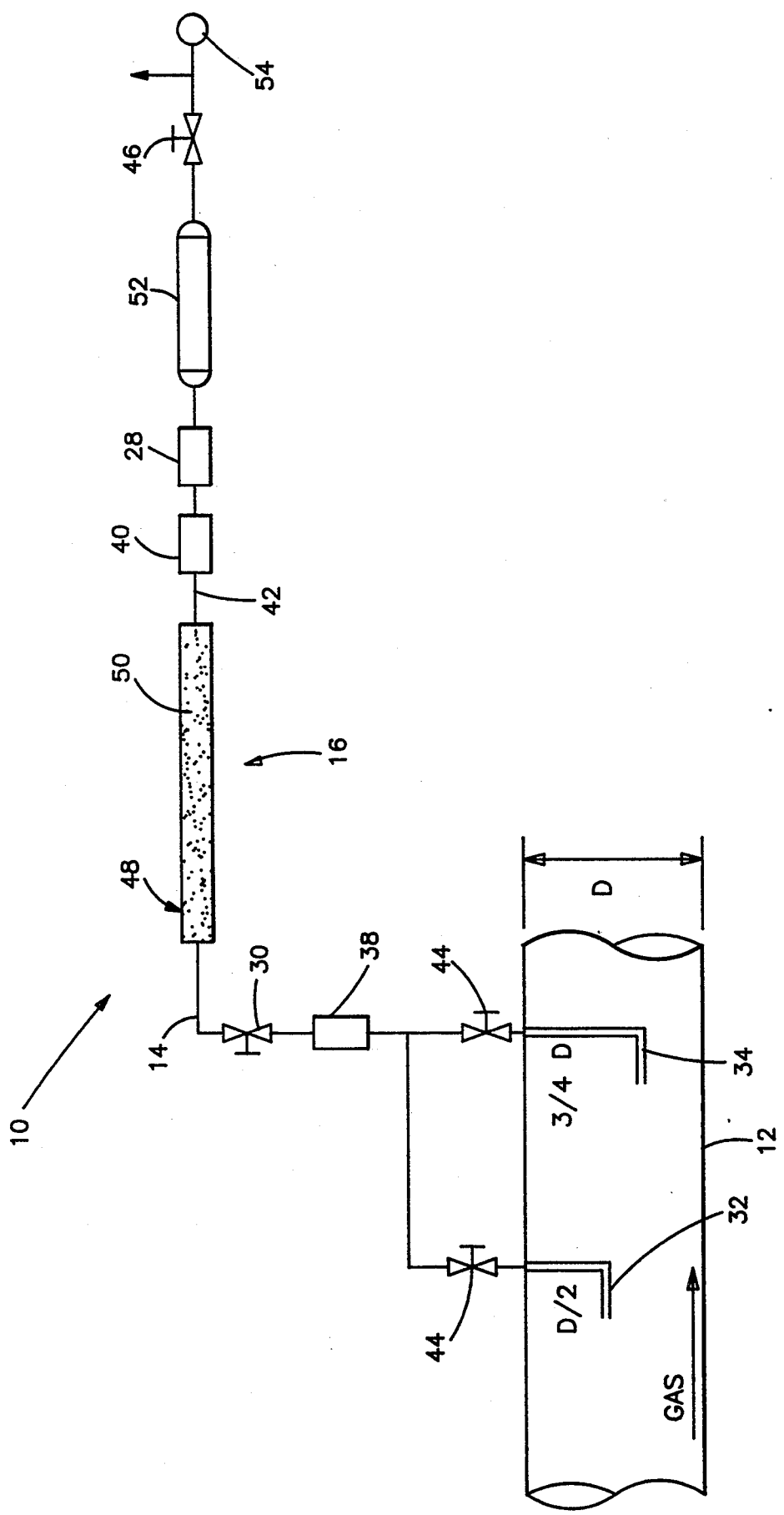
FIG. 2 is a schematic view of an alternate embodiment of the invention.

FIG. 2 illustrates an alternate embodiment of the invention. The majority of elements of this embodiment are identical and/or equivalent in function to those described in the embodiment of FIG. 1. Thus, these elements bear the same reference numerals and repeated descriptions are avoided. The selective trap means 16 of FIG. 2, however, comprises a cylinder 48 containing a porous medium 50. The porous medium 50 is preferably a hydrated aluminum or sand bound with a phenolic resin and polymerized. This porous medium may preferably have a composition as set forth below in Table I.

TABLE I

| Element | Wt. % |
| --- | --- |
| Sand | 95.56% |
| Phenol-Formaldehyde resin | 3.75% |
| Calcium Stearate | 0.50% |
| Hexamine (Hexatetramethylamine) | 0.19% |
| 3-aminepropyltrimethoxysilane | 0.03% |

The phenolic resin may suitably be a novolak resin (a resin catalyzed from an acidic medium). Alternatively, the phenolic resin may be a phenol-formaldehyde resin having a ratio by weight of formaldehyde to phenol of about 0.9. Other examples of suitable resins include VEN-DUR 335, VEN-DUR 520, and VEN-DUR 462, all manufactured by Venezolana de Resinas, C.A.

Porous medium 50 serves to trap crude oil in pore spaces contained within porous medium 50, and also absorbs crude oil. Methods for measuring absorbed/trapped crude oil in this embodiment are described above.

FIG. 2 also illustrates an alternate embodiment of the means for measuring the volume of the gas sample. A container 52 is attached to outlet connector 40, and preferably has a thermocouple 54 or other device for reading the temperature in container 52. The gas sample is introduced into container 52 where the volume can be measured and corrected to a desired temperature.

Note that in the embodiment of FIG. 2, no cooling means are required to obtain selective entrapment of crude oil in porous medium 50.

With reference to the crude and gas volumes determined according to any of the preferred embodiments, the volumes can be corrected to various conditions through the use of familiar pressure/volume/temperature equations and techniques which are well known in the art.

Thus disclosed is a method and apparatus which can be used to obtain accurate and selective readings of the crude oil content of a sample of gas obtained from a gas line.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A method for measuring crude oil contained in a gas flowing in a gas line by measuring the volume of crude oil contained in a sample of the gas, comprising the steps of:

obtaining a sample of gas from said gas line;

passing said sample of gas through means for selectively trapping crude oil so as to trap substantially all crude oil contained in said sample of gas;

measuring the volume of said sample of gas; and measuring the volume of trapped crude oil by measuring the volume of trapped crude oil including the two steps of flushing said selective trap means with a known initial volume of solvent and comparing said known initial volume of solvent to an obtained volume of solvent and crude oil.

2. A method according to claim 1, further including the steps of releasably connecting said selective trap means to a gas line so as to obtain said sample of gas and pass said sample of gas through said selective trap means, disconnecting said selective trap means from said gas line after said sample of gas is passed through said trap means, and transporting said selective trap means to a remote facility where said measuring steps are performed.

3. A method according to claim 1, wherein the step of passing said sample of gas through said selective trap means comprises the steps of passing said sample of gas through means for cooling said sample of gas and then passing said sample of gas through at least one cylinder having filter means for selectively trapping crude oil, whereby substantially all crude oil contained in said sample of gas is trapped.

4. A method according to claim 3, wherein the step of passing said sample of gas through said cooling means comprises the step of passing said sample of gas through a coil submerged in a refrigerated fluid.

5. A method according to claim 4, wherein said step of passing said sample of gas through said cooling means comprises the step of passing said sample of gas through a coil submerged in a fluid refrigerated to a temperature of between about 0°–10° C.

6. A method according to claim 5, wherein the step of passing said sample of gas through at least one cylinder having filter means comprises the step of passing said sample of gas through a plurality of cylinders connected in series after said cooling means, at least a first cylinder of said plurality of cylinders being refrigerated and partially filled with a fluid that is non-soluble with crude oil.

7. A method according to claim 6, wherein said step of passing said sample of gas through a plurality of cylinders includes the step of refrigerating at least said first cylinder to a temperature of between about 0°–10° C.

8. A method according to claim 1, further comprising the step passing said sample of gas through means for detecting crude oil, after passing said sample of gas through said selective trap means, whereby substantial entrapment of crude oil is verified.

9. A method according to claim 1, wherein the step of passing said sample of gas through said selective trap means comprises the step of passing said sample of gas through a polymerized porous medium having a mesh size in a range of about 12–16, said porous medium being bound with a phenolic resin.

* * * * *